United States Patent [19]

Hokama

[11] Patent Number: 4,816,392
[45] Date of Patent: Mar. 28, 1989

[54] RAPID STICK TEST FOR DETECTION OF CIGUATOXIN AND OTHER POLYETHER TOXINS FROM TISSUES

[75] Inventor: Yoshitsugi Hokama, Honolulu, Hi.

[73] Assignee: Research Corporation of the University of Hawaii, Honolulu, Hi.

[21] Appl. No.: 56,130

[22] Filed: Jun. 1, 1987

Related U.S. Application Data

[63] Continuation of Ser. No. 656,934, Oct. 2, 1984, abandoned.

[51] Int. Cl.⁴ ............................................ G01N 33/543
[52] U.S. Cl. ............................................ 435/7; 435/28; 435/188; 435/805
[58] Field of Search .................. 435/7, 28, 188, 805

[56] References Cited

U.S. PATENT DOCUMENTS 4,340,670  7/1982  Mennen .................................. 435/25
4,391,904  7/1983  Litman et al. .......................... 435/7
4,477,576  10/1984  Deutsch et al. ...................... 436/500

OTHER PUBLICATIONS

Schener et al., Science, 155 (1967), 1267-1268.
Hokama et al., Toxicon (1977), vol. 15, pp. 317-325.
Hokama et al., Toxicon (1983), vol. 21, No. 6, 817-824.
Murakami et al., "Bull. Jap. Soc. Sci. Fisheries", (1982), vol. 48(1), 69-72.
Lin et al., J. Am. Chem Soc., 103 (1981), 6773-6775.
Kimura et al., Fed. Am. Soc. Exp. Biol, 67th Ann. Meeting (4/10-4/15/83), Ab. #1952.
Chanteau et al., Chem. Abstracts, 95(11), 1981, #91764C.
Berger et al., Chem. Abstracts, 91(9), 1979, #69378a.

*Primary Examiner*—Christine M. Nucker
*Attorney, Agent, or Firm*—James C. Wray

[57] ABSTRACT

A rapid stick test for the detection of ciguatoxin and other polyether toxins from fish tissue is disclosed. This is a relatively simple and rapid field test utilizing enzyme immunoassay technology for the detection of lipid toxin which can be assessed in ten minutes or less in the field. The invention is both a procedure and a kit for conducting the test. The kit includes a bamboo sampling stick, buffer reagent, anti-ciguatoxin horseradish peroxidase conjugate, substrate reagent, fixation reagent, blotter, filter paper, and medicine dropper.

9 Claims, 1 Drawing Sheet

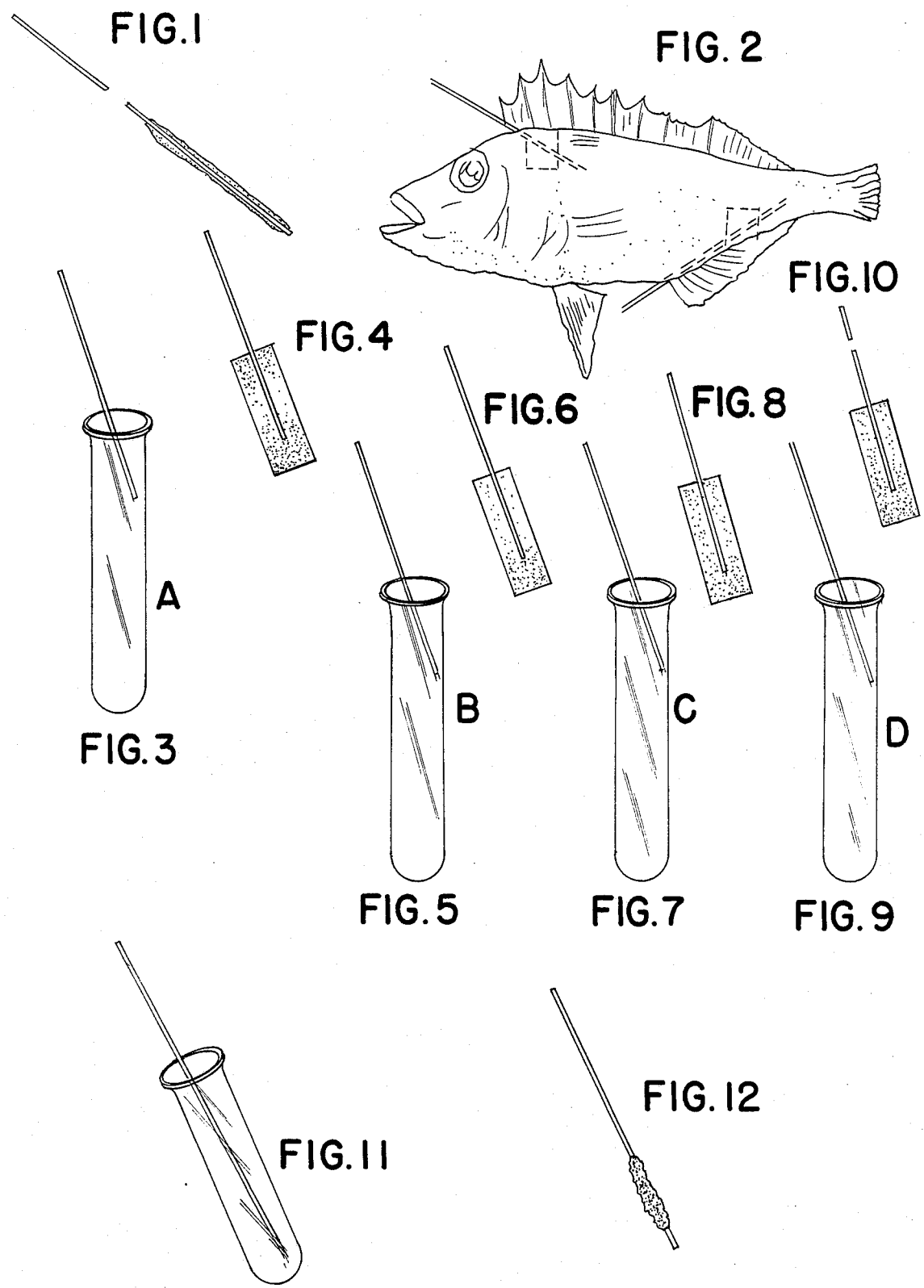

RAPID STICK TEST FOR DETECTION OF CIGUATOXIN AND OTHER POLYETHER TOXINS FROM TISSUES

This application is a continuation of application Ser. No. 656,934, filed Oct. 2, 1984 abandoned.

TECHNICAL FIELD

The invention relates to chemistry, especially molecular biology and microbiology, as well as to analytical and immunological testing. More in particular, the invention relates to measuring or testing processes involving enzymes or microorganisms wherein test strips are used in this process. The test strips are used in conjunction with anitbody binding assays and antigen antibody reactions. These reactions may involve immune complexes formed in liquid phase. The antibodies used may be monoclonal antibodies and separation techniques for removing immune complexes from unbound antigen or antibodies are used. Apparatus in such areas come under the heading of physical support structures such as tubes, bottles, or dipsticks. These tests may be in automated modes or in compartmentalized kits.

BACKGROUND ART

Competitive binding assays are well known and well used tools in the clinical arena. They provide a specificity and sensitivity necessary for accurate qualitative and quantitative determinations. The art is full of examples of radioimmunoassays and more recently enzyme immunoassays. In the realm of enzyme immunoassays the enzyme horseradish peroxidase is a popular tag for antibodies as it is economically attractive as well as easily attachable to antibodies. The dipstick enzyme immunoassay test is used for rapid qualitating and semi-quantitating the presence of an analyte. These tests, which have become more and more popular are probably an outgrowth from the urinalysis dipstick test.

DISCLOSURE OF INVENTION

A long felt need has existed in the prior art for a rapid method distinguishing edible fishes from potentially toxic fishes. The fish of concern are those found near shore which contain the substance known as ciguatoxin and/or polyether. Ciguatoxin is a marine saponin of unknown structure, but with the empirical formula $C_{35}H_{65}NO_8$. Essentially this toxin is a nitrogenous glycocide found in certain fish and possesses the common property of foaming or making suds when strongly agitated in aqueous solution. This toxin can hold resinous and fatty substances in suspension in water, and can be highly irritating when in contact with the skin or mucous membranes and if taken internally can cause nausea and vomiting. The ingestion of a fish or tissue from a fish containing this substance results in a condition known as ciguatera, and the symptoms are gastrointestinal upset, muscular weakness, as well as other neurological disturbances.

Therefore, it is an object of this invention to provide a rapid method for the detection of the presence of ciguatoxin and other polyether toxins from the tissues of fish. It is also an object of this invention that such a test be rapid and easily performed such that any lay person may use this method for sorting edible from potentially toxic fishes. It is also an object of this invention to provide a kit such that this method may be performed on site.

The method is very simple. It is a rapid field stick enzyme immunoassay test for the detection of ciguatoxin and related polyether marine toxins from fish tissue. It is a field test procedure and basically, a bamboo stick with a LIQUID PAPER brand correction fluid coating is inserted into the fish tissue about an inch and rotated into the upper portion near the head region of the fish. The stick is then removed and dried. Preferably, another stick containing the correction fluid coating is inserted in a similar manner near the mid-line of the fish toward the tail end. After drying these sticks, the sticks are then fixed in a solution of methyl alcohol and hydrogen peroxide for about five seconds. This solution is contained in vial A. After blotting the sticks, the coated portion of the stick is immersed in a buffer contained in vial B and removed after ten seconds. The sticks are touched to filter paper so as to remove any excess buffer. The coated portion of the stick is then immersed in vial C containing an antibody and enzyme conjugate known as anti-ciguatoxin horseradish peroxidase for fifteen seconds, removed, and touched to filter paper to remove any excess. The coated portion of the stick is then rinsed in the buffer contained in vial B for about fifteen seconds, then touched to filter paper to remove any excess buffer. The coated portion of the stick is immersed into a test tube containing ten drops of substrate. The test tube is slanted so as to cover the stick with the substrate solution and the tube is shaken vigorously to make good contact between the stick and the solution. This substrate is contained in vial D and is 4-chloro-1-naphthol, distilled water and hydrogen peroxide. The substrate in the test tube is then compared to a color chart within ten minutes of coming into contact with the stick. The color of the substrate is then given a number corresponding to the color on the color chart, and if that number is between 0 and 2, the test is negative. If the number is 3 to less than 4, the test is borderline, and if the number is equal to or greater than 4, the test is positive. All color reactions equal to or greater than 4 should not be eaten. Three to less than 4 may be eaten, but at one's own risk. Less than 3 may be eaten, and less than 2.5, the fish is deemed edible.

The kit consists esentially of tissue sampling bamboo sticks for stabbing tissue and retrieving a sample thereof. It also contains five vials which represent the various stations one must dip the tissue sample in, in order to obtain results.

BRIEF DESCRIPTION OF THE DRAWINGS

FIG. 1 is a perspective of the dipstick with a liquid paper coating.

FIG. 2 is a side view showing the insertion of the dipsticks.

FIG. 3 shows the dipstick immersed in vial A.

FIG. 4 shows the blotting of the dipstick.

FIG. 5 shows the dipstick immersed in vial B.

FIG. 6 shows the touching of the dipstick to filter paper.

FIG. 7 shows the dipstick immersed in vial C.

FIG. 8 shows the dipstick being touched to a filter paper.

FIG. 9 shows the dipstick immersed in vial D.

FIG. 10 shows the dipstick being touched to filter paper.

FIG. 11 shows the dipstick immersed in a vial containing substrate and being shaken.

FIG. 12 is another perspective of the dipstick.

DETAILED DESCRIPTION OF THE INVENTION

The FIGS. 1 through 11 show the performance of the rapid field stick enzyme immunoassay test for detection of ciguatoxin and related polyether marine toxins from fish tissue. In FIG. 1 the tissue collecting stick is shown with a correction fluid coating.

In FIG. 2 the coated end of the bamboo sticks are shown in their preferred sampling sites within the fish to be tested.

FIG. 3 represents fixing the tissue upon the coated end of the dipstick in vial A.

FIG. 4 represents a technique for removing any excess fixative which may remain upon the stick after being removed from vial A. It is preferred that the stick be touched or blotted by filter paper.

FIG. 5 shows the next step wherein the dipstick is immersed in a buffer, and then it has the excess buffer removed by touching the coated end of the stick to a filter paper as shown in FIG. 6.

FIG. 7 shows the immersion of the coated end of the stick into vial C containing the anti-ciguatoxin horseradish peroxidase conjugate, and FIG. 8 shows the removing of the excess of that conjugate by touching the coated end of the dipstick to a filter paper.

FIG. 9 shows the rinsing of the dipstick in vial D containing the buffer, and FIG. 10 shows the removing of the excess buffer by touching the dipstick to a filter paper.

FIG. 11 shows the dipstick being immersed and shaken within a vial containing substrate wherein the substrate may or may not form a color reaction. This color reaction then will be compared to a chart wherein determinations of qualitative and semi-quantitative natures are made.

Having described the procedure, the best mode for the rapid field stick enzyme immunoassay test for detection of ciguatoxin and related polyether marine toxins from fish tissue is now described. The field kit consists of tissue sampling sticks, five reagent vials, a medicine dropper, test tubes, blotter and filter paper. The sticks are preferably made of bamboo and have one end coated with correction fluid. These sticks are then used to stab fish tissue whereupon toxins within the tissue are absorbed by the coating on the end of the stick.

Vial A contains a fixation reagent, and it is preferred that this reagent consist of 99.7 percent methyl alcohol and 0.3 percent hydrogen peroxide. Vial B contains a buffer known as Tris. This is a weak basic compound extensively used as a buffer in enzymic reactions. Its organic chemistry nomenclature is 2-amino-2-(hydroxymethyl)-1,3-propanediol. The pH of the Tris is $7.5 +/- 0.05$ and the buffer contains 0.01 percent sodium azide (NaN3). The sodium azide serves as a preservative and inhibits catalase.

Vial C contains the conjugate of anti-ciguatoxin horseradish perioxidase. This reagent consists of preferably monoclonal antibody to ciguatoxin and other polyether toxins. It is preferred that the antibody, anti-ciguatoxin be a monoclonal antibody directed to recognizing ciguatoxin and related polyether marine toxins, and this antibody may be produced by any conventional hybridoma technology. The antibody is tagged with the enzyme horseradish peroxidase and together the anti-ciguatoxin horseradish peroxidase is considered to be a conjugate. This reagent along with the buffer reagent of vial B is preferably stored in lyophilized form at four degrees centigrade. The stability of buffers stored in lyophilized fashion is eight months and once reconstituted with fifteen mls of distilled water it is stable for one month. The stability of the conjugate in lyophilized form is eight months and once reconstituted is stable for one day.

Vial D contains a substrate which in this case is 4-chloro-1-naphthol. As with vial B and vial C, it is preferred that this sample be stored in lyophilized form and stored at four degrees centrigrade. It may be reconstituted with 15 mls of distilled water and thirty drops (1.5 ml) of three percent hydrogen peroxide (H2O2) solution. The stability of vial D in lyophilized form is eight months, and once reconstituted, one day. This substrate is a substance acted upon and changed by the enzyme horseradish peroxidase.

Vial E contains the distilled water used to reconstitute the lyphilized reagents in the other vials.

The basic theory of the test is that toxins in suspect tissue are absorbed by the correction fluid coated on the end of the bamboo stick. The stick dried and then fixed with a fixation reagent. This fixations is critical in that it effects the rapid killing of tissue elements and their preservation and hardening, to retain as nearly as possible the same relations they had in the living tissue. Once fixed the coated end of the bamboo stick is then blotted to remove the excess fixation reagent, and then the stick is immersed in the buffer for about ten seconds. The buffer is absorbed onto the coated end of the stick and sets up a favorable environment for an enzyme immunoreaction. Any excess bubber is removed by touching the coated end of the bamboo stick to filter paper. Next the stick is inserted into the conjugate. If the fish tissue contains ciguatoxin or related polyether marine toxins, the conjugate will attach thereto. The stick is then touched to a filter paper to remove any excess conjugate, and then the stick is rinsed in the buffer. This step is to remove any unboard conjugate. The last step is to immerse the coated end of the bambo stick into substrate for the enzyme. If there was ciguatoxin or related polyether marine toxins in the fish, then they were absorbed onto the stick and they bound the conjugate. The bound conjugate will react with the substrate in direct proportion with the amount of bound conjugate on the coated end of the bamboo stick. The substrate will change color upon reacting with the enzyme and the amount of color change will be directly proportional to the amount of toxin within the fish. The substrate is then compared to a color chart and assigned a number. This number is then used to determine whether or not the fish is edible. All color reactions equal to or greater than 4 should not be eaten. If the number is 3 to just short of 4, the fish may be eaten but at one's own risk. If the number is less than 3, the fish may be eaten, and if the number is 2.5 the fish is considered edible. It should be noted that different people can tolerate different levels of toxins, but if the number is less than 2.5 the fish is considered palatable. Above 2.5 there are varying degrees of toxicity, and if the reaction is greater than 4, the fish is absolutely inedible.

"Correction fluid" is a generic name for a product which is well known and widely used. LIQUID PAPER is a brand name of correction fluid and is made by Liquid Paper Corporation of Boston, Mass. As is well known, correction fluid is applied as a fluid but dries hard almost instantly. LIQUID PAPER brand correction fluid is an organic soluble material consisting essentially of trichloroethylene, 1,1,1-trichloroethane, titanium dioxide, resins, dispersants and colorants.

What I claim is:

1. The method for detection of ciguatoxin and structually related polyether marine toxins in fish tissue, comprising the steps of:
   (a) inserting a coated portion of a bamboo stick coated with an absorbent coating into suspect tissue;
   (b) withdrawing said stick;
   (c) air drying said stick;
   (d) immersing the dried stick in a fixature fluid consisting essentially of methyl alcohol;
   (e) blotting said stick to remove excess fixative fluid;
   (g) removing excess buffer;
   (h) immersing said stick into anti-ciguatoxin horseradish peroxidase conjugate consisting of an antibody directed to recognizing ciguatoxin and related polyether marine toxins and tagged with an enzyme horseradish peroxidase, wherein the subject toxins, if present, attach to the conjugate;
   (i) immersing said stick in said buffer to remove unbound conjugate;
   (j) removing excess of said buffer;
   (k) immersing said stick into enzyme substrate, 4-chloro-1-naphthol, for approximately ten minutes;
   (l) removing said stick from said substrate;
   (m) observing color change of said substrate to determine presence of subject toxins.

2. The method of claim 1 wherein said inserting occurs by imbedding the coated end of said bamboo stick into fish tissue about an inch and rotating said stick, whereby said stick is coated with any toxin present within the fish tissue.

3. The method of claim 1 wherein the fixative fluid comprises 99.7 percent absolute methyl alcohol and 0.3 percent hydrogen peroxide.

4. The method of claim 1 wherein the buffer reagent comprises 0.05 M Tris (hydroxymethyl) aminomethane, pH 7.5+/−0.05 containing 0.01 percent human serum albumin and 0.01 percent sodium azide, for five to ten seconds.

5. The method of claim 1 wherein said removing of excess buffer occurs by touching said coated end of the bamboo stick to filter paper.

6. The method of claim 1 further comprising, after step (a) and before step (b), rotating said stick, wherein the point of insertion is in the upper portion of the fish body near the head of the fish.

7. The method of claim 1 wherein the immersing of step (h) is for about fifteen seconds.

8. The method of claim 1 wherein the immersing of step (f) is for about ten seconds.

9. A kit for field testing fish for the presence of ciguatoxin and structurally related polyether marine toxins comprising,
   at least one tissue sampling stick, each having an end portion coated with a specific extractant for subject toxins, the coated end being insertable into fish tissue to absorb toxins,
   a vial of fixation reagent for fixing toxins on the coated end portion of the stick.
   a vial of buffer for conditioning the fixed coated end portion to facilitate an enzyme immuno-reaction,
   a vial of conjugate which includes an enzyme and an antibody specific to the subject toxins, for containing the buffered end portion, whereby antibody binds to the subject toxins, and
   a vial of substrate for the enzyme, whereby the conjugate reacts with the substrate to cause a color change in the substrate in the presence of toxins.

* * * * *